United States Patent
Suguri et al.

(10) Patent No.: US 12,091,379 B2
(45) Date of Patent: Sep. 17, 2024

(54) PRODUCT 1,3-BUTYLENE GLYCOL

(71) Applicant: KH Neochem Co., Ltd., Tokyo (JP)

(72) Inventors: Akihiro Suguri, Mie (JP); Tomohiro Iwasa, Mie (JP); Takashi Hakumura, Mie (JP); Jun Kanada, Mie (JP)

(73) Assignee: KH NEOCHEM CO., LTD., Tokyo (JP)

( * ) Notice: Subject to any disclaimer, the term of this patent is extended or adjusted under 35 U.S.C. 154(b) by 0 days.

(21) Appl. No.: 18/018,752

(22) PCT Filed: May 18, 2022

(86) PCT No.: PCT/JP2022/020607
§ 371 (c)(1),
(2) Date: Jan. 30, 2023

(87) PCT Pub. No.: WO2022/244791
PCT Pub. Date: Nov. 24, 2022

(65) Prior Publication Data
US 2023/0227389 A1    Jul. 20, 2023

(30) Foreign Application Priority Data
May 18, 2021    (JP) .................................. 2021-084070

(51) Int. Cl.
*C07C 31/20* (2006.01)
*C07C 29/09* (2006.01)
(Continued)

(52) U.S. Cl.
CPC ............ *C07C 31/207* (2013.01); *C07C 29/09* (2013.01); *C07C 29/74* (2013.01); *C07C 29/80* (2013.01); *C07C 29/84* (2013.01); *C07C 29/86* (2013.01)

(58) Field of Classification Search
CPC ....... C07C 31/207; C07C 29/09; C07C 29/60; C07C 29/80; C07C 29/84; C07C 29/86
See application file for complete search history.

(56) References Cited

U.S. PATENT DOCUMENTS

| 3,816,549 | A | * | 6/1974 | Prinz ....................... C07C 31/20 |
| | | | | 568/868 |
| 6,376,725 | B1 | * | 4/2002 | Tsuji ....................... C07C 31/20 |
| | | | | 568/853 |

(Continued)

FOREIGN PATENT DOCUMENTS

| CN | 1558890 A | 12/2004 |
| CN | 108383684 A | 8/2018 |

(Continued)

OTHER PUBLICATIONS

CN 110790634, Chen Yong, et al, Preparation method of 1,3-butanediol, 1 page abstract. (Year: 2020).*

(Continued)

*Primary Examiner* — Yate' K Cutliff
(74) *Attorney, Agent, or Firm* — Sterne, Kessler, Goldstein & Fox P.L.L.C.

(57) ABSTRACT

A product 1,3-butylene glycol, in which 2,4-dinitrophenyl-hydrazine derivatives of 2-(hydroxyethyl)-2,6-dimethyl-1,3-dioxane have a weight proportion of 90 ppm or less, as calculated from a sum of absorbance of peaks thereof in an HPLC analysis under specific conditions after specific sample preparation.

6 Claims, 1 Drawing Sheet

(51) Int. Cl.
    *C07C 29/74*  (2006.01)
    *C07C 29/80*  (2006.01)
    *C07C 29/84*  (2006.01)
    *C07C 29/86*  (2006.01)

(56) References Cited

U.S. PATENT DOCUMENTS

| | | | |
|---|---|---|---|
| 8,445,733 B1 | 5/2013 | Windhorst et al. | |
| 2004/0254407 A1* | 12/2004 | Mizutani | C07C 29/80 568/852 |
| 2021/0101855 A1 | 4/2021 | Khandurina et al. | |
| 2023/0087989 A1* | 3/2023 | Shimizu | C07C 31/207 424/401 |

FOREIGN PATENT DOCUMENTS

| | | | | |
|---|---|---|---|---|
| CN | 110790634 A | * | 2/2020 | ............ B01J 23/002 |
| CN | 114901625 A | | 8/2022 | |
| EP | 1046628 A1 | * | 10/2000 | ............ C07C 29/141 |
| EP | 1437337 A1 | * | 7/2004 | ............ C07C 29/80 |
| EP | 4026823 A1 | | 7/2022 | |
| JP | 2003096006 | | 4/2003 | |
| JP | 2003-252811 | | 9/2003 | |
| JP | 2020-512351 A | | 4/2020 | |
| JP | 6804601 | | 12/2020 | |
| KR | 20190023466 A | | 3/2019 | |
| WO | WO 00/07969 | | 2/2000 | |
| WO | WO-2013183592 A1 | * | 12/2013 | ............ B01D 3/002 |
| WO | WO2021132369 | * | 7/2021 | ............ C07C 31/20 |

OTHER PUBLICATIONS

WO2013/183592, Mitsubishi Chem. Corp., Production Method for 1,4-butanediol, English translation, 32 pages (Year: 2013).*

International Search Report of the International Searching Authority directed to related International Patent Application No. PCT/JP2022/020607, mailed Jul. 19, 2012, with attached English-language translation; 4 pages.

Decision to Grant from priority Japanese patent application No. 2021-084070, dated Mar. 23, 2022, and machine translation, 5 pages.

Notice of Reasons for Refusal from priority Japanese patent application No. 2021-084070, dated Dec. 1, 2021, and machine translation, 6 pages.

* cited by examiner

PRODUCT 1,3-BUTYLENE GLYCOL

TECHNICAL FIELD

The present invention relates to a product 1,3-butylene glycol that is useful as a raw material of synthetic resins, a raw material of surfactants, a solvent, an antifreeze, a cosmetic raw material or the like.

BACKGROUND ART 1,3-Butylene glycol is a viscous, colorless, transparent and odorless liquid having a boiling point of 208° C. and has excellent chemical stability. Therefore, 1,3-butylene glycol is used as a raw material of a variety of synthetic resins and surfactants. 1,3-Butylene glycol is also in use as a material for cosmetics, moisture absorbers, high-boiling point solvents and antifreezes due to its excellent moisture absorption characteristic, low volatility and low toxicity. Particularly, in recent years, the demand for 1,3-butylene glycol has been significantly growing in the cosmetic industry since non-toxic and no-stimulus 1,3-butylene glycol has excellent properties as a moisturizer.

Patent Literature 1 discloses 1,3-butylene glycol having a weak odor. Furthermore, as a method for obtaining 1,3-butylene glycol having a weak odor, a production method of 1,3-butylene glycol including a step of mixing crude 1,3-butylene glycol with water and an organic solvent, phase-separating the mixture into a water layer and an organic layer and then obtaining a water layer containing 1,3-butylene glycol is disclosed. In the production method of the same literature, as the organic solvent that is used as an extraction solvent, ketones are considered to be favorable, and methyl isobutyl ketone is considered to be more preferable.

CITATION LIST

Patent Literature

Patent Literature 1: Japanese Patent Laid-Open No. 2003-96006

SUMMARY OF INVENTION

Technical Problem

However, in the method described in Patent Literature 1, there is a problem in that it is difficult to completely remove the odor and thus, when 1,3-butylene glycol is stored for a long period of time, a slight odor is generated due to a change over time.

Additionally, in the cosmetics field, there are cases where 1,3-butylene glycol is heated and blended under a basic condition during use, but 1,3-butylene glycol that is obtained by the method described in Patent Literature 1 has a problem of coloration when mixed and prepared under a basic condition.

In consideration of the above-described circumstances, an objective of the present invention is to provide a product 1,3-butylene glycol that is odorless, generates no odors over time and, additionally, does not easily color under a basic condition.

Solution to Problem

As a result of intensive studies, the present inventors have found that the above-described problems can be solved by suppressing the concentration of a specific impurity that is contained in 1,3-butylene glycol at a certain level or lower and have completed the present invention.

More specifically, the present invention is as described below.

[1]

A product 1,3-butylene glycol, wherein 2,4-dinitrophenylhydrazine derivatives of 2-(hydroxyethyl)-2,6-dimethyl-1,3-dioxane have a weight proportion of 90 ppm or less, as calculated from a sum of absorbance of peaks thereof in an HPLC analysis under the following conditions after the following sample preparation, wherein the sample preparation is as follows:
1000 μL of a solution of 2,4-dinitrophenylhydrazine which is extracted by adding 5 mL of acetonitrile to a 2,4-dinitrophenylhydrazine cartridge (InertSep mini AERO DNPH, GL Sciences Inc.) and 100 μL of 0.2 mol/L hydrochloric acid are added to 0.05 g of the product 1,3-butylene glycol and reacted at 45° C. for two hours, and wherein the conditions of HPLC analysis are as follows:
Measurement sample: a reaction liquid obtained by the sample preparation is diluted to 2 mL with a mobile phase that is used in HPLC, and the diluted liquid is used as a measurement sample,
Detector: UV-Vis detector,
Detection wavelength: 369 nm,
Analysis column: a column in which palmitamidopropyl group-modified silica gel (particle diameter: 5 μm, inner diameter×length=4.6 mm×25 cm, pore size: 100 Å, surface coating level: 2.7 μmol/m$^2$, surface area: 450 m$^2$/g, metal impurity: less than 5 ppm, carbon content: 19.5%) is used as a stationary phase,
Analysis condition: column temperature of 40° C.,
Mobile phase: acetonitrile/distilled water=50/50 (volume ratio),
Mobile phase flow rate: 0.4 mL/min.,
Sample injection amount: 20 μL,
Calibration curve: created using separately synthesized dinitrophenylhydrazine derivatives of 2-(hydroxyethyl)-2,6-dimethyl-1,3-dioxane.

[2]

The product 1,3-butylene glycol according to [1], wherein the 2,4-dinitrophenylhydrazine derivatives of 2-(hydroxyethyl)-2,6-dimethyl-1,3-dioxane have a weight proportion of 75 ppm or less, as calculated from the sum of the absorbance of the peaks thereof.

[3]

The product 1,3-butylene glycol according to [1] or [2], wherein the 2,4-dinitrophenylhydrazine derivatives of 2-(hydroxyethyl)-2,6-dimethyl-1,3-dioxane have a weight proportion of 60 ppm or less, as calculated from the sum of the absorbance of the peaks thereof.

Advantageous Effects of Invention

The present invention makes it possible to provide a product 1,3-butylene glycol that is odorless, generates no odors over time and, additionally, does not easily color under a basic condition.

DESCRIPTION OF EMBODIMENTS

Figure 1:
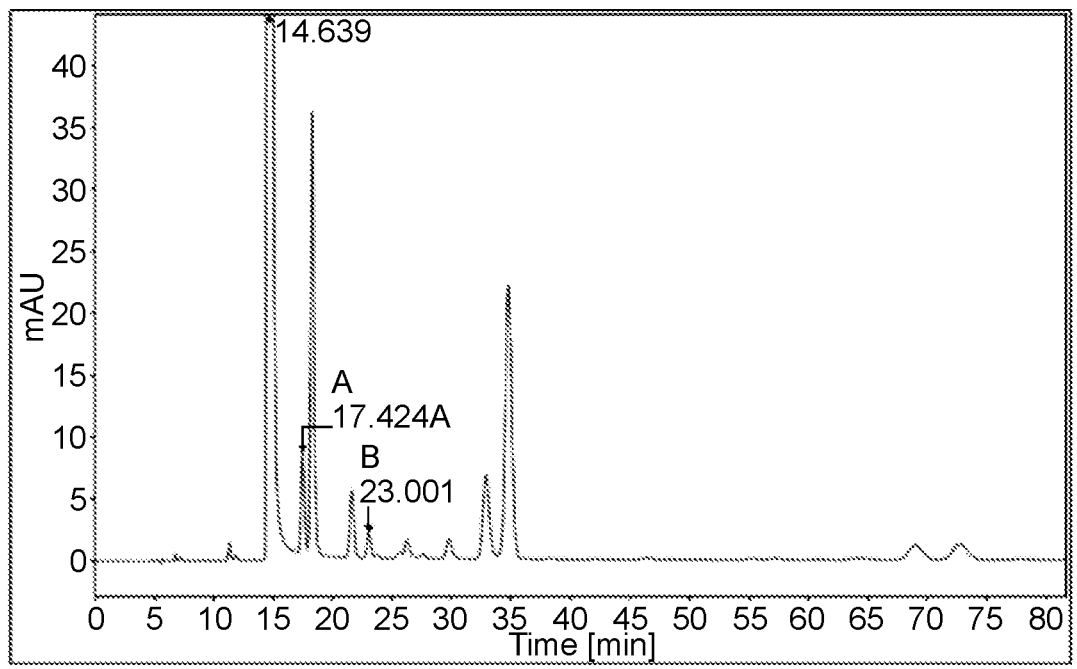
FIG. 1 is a chart of an HPLC analysis of 1,3-butylene glycol in Example 1 after being reacted by a 2,4-dinitrophenylhydrazine reagent in advance.

Hereinafter, an embodiment of the present invention (hereinafter, referred to as "present embodiment") will be described in detail. The present invention is not limited to the following description and can be carried out after being modified in a variety of manners within the scope of the gist thereof.

In the present embodiment, 1,3-butylene glycol that is the final product will be also referred to as "product 1,3-butylene glycol", and 1,3-butylene glycol as a raw material will be also referred to as "crude 1,3-butylene glycol".

A product 1,3-butylene glycol according to the present embodiment is a product 1,3-butylene glycol in which the weight proportion that is calculated from the sum of the absorbance of peaks of 2,4-dinitrophenylhydrazine derivatives of 2-(hydroxyethyl)-2,6-dimethyl-1,3-dioxane in an HPLC analysis under specific conditions after being reacted by a 2,4-dinitrophenylhydrazine reagent in advance (hereinafter, also simply referred to as "peak sum weight proportion") is 90 ppm or less. The 2,4-dinitrophenylhydrazine derivatives of 2-(hydroxyethyl)-2,6-dimethyl-1,3-dioxane are 2,4-dinitrophenylhydrazine (hereinafter, also referred to as "DNPH")-derivatized compounds from an impurity that is contained in 1,3-butylene glycol. Regarding these compounds, in an HPLC analysis under specific conditions to be described below, the peaks of the derivatives appear as a peak A and a peak B (refer to FIG. 1 and FIG. 2) within a relative retention time range of 1.1 to 1.6 when the relative retention time of the peak of DNPH is regarded as 1.0.

The measurement conditions of the HPLC analysis in the present embodiment are as described below.
Sample Preparation 1000 μL of a solution from which 2,4-dinitrophenylhydrazine has been extracted by adding 5 mL of acetonitrile to a 2,4-dinitrophenylhydrazine cartridge (InertSepmini AERO DNPH, GL Sciences Inc.) and 100 μL of 0.2 mol/L hydrochloric acid are added to 0.05 g of the product 1,3-butylene glycol and reacted at 45° C. for two hours.
Conditions of HPLC Analysis Measurement sample: A reaction liquid that is obtained by the sample preparation is diluted to 2 mL with a mobile phase that is used in HPLC, and this diluted liquid is used as a measurement sample.

Detector: UV-Vis detector

Detection wavelength: 369 nm

Analysis column: A column in which palmitamidopropyl group-modified silica gel (particle diameter: 5 μm, inner diameter×length=4.6 mm×25 cm, pore size: 100 Å, surface coating level: 2.7 μmol/m$^2$, surface area: 450 m$^2$/g, metal impurity: less than 5 ppm, carbon content: 19.5%) is used as a stationary phase Analysis condition: Column temperature of 40° C.

Mobile phase: acetonitrile/distilled water=50/50 (volume ratio)

Mobile phase flow rate: 0.4 mL/min.

Sample injection amount: 20 μL

Calibration curve: Created using separately synthesized dinitrophenylhydrazine derivatives of 2-(hydroxyethyl)-2,6-dimethyl-1,3-dioxane Here, as the analysis column, for example, SUPELCO (R) Ascentis (R) RP-Amide (particle diameter: 5 μm, inner diameter×length=4.6 mm×25 cm) manufactured by Merck KGaA can be used.

In the measurement of the sample prepared by the above-described method, the absorbance at 369 nm of the peaks of the dinitrophenylhydrazine derivatives of 2-(hydroxyethyl)-2,6-dimethyl-1,3-dioxane are measured with an ultraviolet spectrophotometer. The sum of the obtained absorbance is converted to the weight proportion of the dinitrophenylhydrazine derivatives of 2-(hydroxyethyl)-2,6-dimethyl-1,3-dioxane in 1,3-butylene glycol using "peak sum weight proportion (ppm)=coefficient×sum of absorbance", which is a formula derived with the calibration curve.

When the peak sum weight proportion is 90 ppm or less, the generation of an odor and coloration under a basic condition of the product 1,3-butylene glycol are reduced.

The peak sum weight proportion is preferably 75 ppm or less, more preferably 60 ppm or less, still more preferably 44 ppm or less and particularly preferably 30 ppm or less from the viewpoint of the effect of the present invention becoming more significant. The lower limit of the weight proportion is not particularly limited and may be, for example, 1 ppm or more from the viewpoint of the production cost.

In the HPLC analysis under the above-described conditions, the relative retention time of the dinitrophenylhydrazine derivatives of 2-(hydroxyethyl)-2,6-dimethyl-1,3-dioxane can be confirmed by, for example, adding 100 μL of 0.2 mol/L hydrochloric acid and 1000 μL of a solution extracted by adding 5 mL of acetonitrile to a DNPH cartridge (InertSep mini AERO DNPH, GL Sciences Inc.) to 0.05 g of a solution diluted with 1,3-butylene glycol manufactured by KH Neochem Co., Ltd. such that the weight concentration of separately synthesized 2-(hydroxyethyl)-2,6-dimethyl-1,3-dioxane reaches 300 ppm, reacting the components at 45° C. for two hours, diluting an obtained reaction liquid with a mobile phase that is used in the HPLC analysis to 2 mL and measuring the peaks of the dinitrophenylhydrazine derivatives of 2-(hydroxyethyl)-2,6-dimethyl-1,3-dioxane in the HPLC analysis under the above-described conditions.

In the product 1,3-butylene glycol of the present embodiment, the area percentage of the peak of 1,3-butylene glycol in a gas chromatography analysis under the following conditions is not particularly limited, but is, for example, preferably 99.5% or more, more preferably 99.7% or more, still more preferably 99.8% or more and particularly preferably 99.9% or more depending on required product qualities.

The measurement conditions of the gas chromatography analysis in the present embodiment are preferably as described below.
Conditions of Gas Chromatography Analysis Analysis column: A column in which a stationary phase is dimethylpolysiloxane (length 30 m×inner diameter 0.25 mm×film thickness 0.25 μm)

Temperature rising conditions: The temperature is raised from 80° C. up to 230° C. at 5° C./minute and then retained at 230° C. for 10 minutes.

Sample introduction temperature: 250° C.

Carrier gas: Nitrogen

Gas flow rate in column: 0.5 mL/minute

Detector and detection temperature: Flame ionization detector (FID), 250° C.
Coloration Under Basic Condition The product 1,3-butylene glycol in the present embodiment has an advantage of not easily coloring under a basic condition. The color saturation (b*) of the CIE color space (JIS Z 8729) of the product 1,3-butylene glycol of the present embodiment after being heated under a basic condition at 90° C. for six hours is not particularly limited; however, for example, the average value of three times of measurement is preferably 4.4 or less, more preferably 4.1 or less and particularly preferably 3.8 or less.

Production Method of Product 1,3-Butylene Glycol

Raw Material

Crude 1,3-butylene glycol that is used as a raw material at the time of producing the product 1,3-butylene glycol in the present embodiment is not particularly limited, and examples thereof include 1,3-butylene glycol from which an odor is sensed or 1,3-butylene glycol the odor of which becomes stronger over time. Alternatively, examples thereof also include 1,3-butylene glycol that colors during preparation under a basic condition.

As the crude 1,3-butylene glycol as the raw material, the area percentage of the peak of 1,3-butylene glycol in a gas chromatography analysis under the above-described specific conditions is preferably 99.5% or more, more preferably 99.6% or more and still more preferably 99.7% or more from the viewpoint of reducing the amount of impurities that is contained in the product 1,3-butylene glycol.

A production method of the crude 1,3-butylene glycol as the raw material is not particularly limited, and the crude 1,3-butylene glycol can be produced by, for example, a well-known method (refer to Japanese Patent Publication No. H3-80139, Japanese Patent Laid-Open No. H7-258129 and the like). In addition, any of crude 1,3-butylene glycol produced by a liquid phase hydrogen reduction method of acetaldol, crude 1,3-butylene glycol produced by a hydrolysis method of 1,3-butylene oxide, crude 1,3-butylene glycol produced by a fermentation method in which a microbe or a fungus is used, a mixture thereof and the like may also be used. Among these, a reaction product obtained by the liquid phase hydrogen reduction method of acetaldol is preferably used since there is a tendency that the effect of the present invention becomes more significant. In the liquid phase hydrogen reduction method of acetaldol, low-boiling compounds such as acetaldehyde, butyraldehyde, crotonaldehyde, methyl vinyl ketone or 2-(hydroxyethyl)-2,6-dimethyl-1,3-dioxane, which are considered to be odor-causing substances, condensates of the low-boiling compounds, acetals of the low-boiling compounds and 1,3-butylene glycol, acetals of the low-boiling compounds and ethanol or the like are generated as byproducts, and it is difficult to completely remove the low-boiling compounds or the like even by distillation. As the odor-causing substances, substances that act as odor sources, substances that turn into odor substances due to a change over time, a heating treatment, a chemical treatment or the like and the like are included.

The reaction product that is obtained by a hydrogen reduction method of acetaldol may also be used after alcohols such as ethanol, salts, moisture or the like, which are byproducts, are removed. A method for removing the above-described components is not limited, and a method such as distillation or adsorption can be used.

In addition, the reaction product that is obtained by the hydrogen reduction method of acetaldol from which ethanol or the like, which is a byproduct, has been removed by distillation or a substance obtained by further performing one or more well-known purification steps, for example, a step of adding an alkali metal compound (for example, sodium hydroxide, potassium hydroxide or the like) and performing a heating treatment (refer to Japanese Patent No. 4559625 or the like) on a distillate from which ethanol has been removed may also be used as the crude 1,3-butylene glycol. The crude 1,3-butylene glycol can also be procured as a commercially available product.

A production method of the product 1,3-butylene glycol in the present embodiment is not particularly limited, and it is possible to use, for example, a method including a step of mixing the crude 1,3-butylene glycol with water and an organic solvent, phase-separating the mixture into a water layer and an organic layer and then obtaining a water layer containing 1,3-butylene glycol (extraction step), a step of performing a heating treatment on the water layer containing 1,3-butylene glycol (hydrolysis step), a step of distilling water away from the water layer containing 1,3-butylene glycol that has been subjected to the heating treatment (dehydration with distillation step) and a step of distilling low-boiling point components away from 1,3-butylene glycol from which water has been distilled away (low-boiling fraction distillation step). Hereinafter, each step will be described.

Extraction Step

The extraction step in the production method of the product 1,3-butylene glycol of the present embodiment is a step of mixing the crude 1,3-butylene glycol with water and an organic solvent, phase-separating the mixture into a water layer and an organic layer and then obtaining a water layer containing 1,3-butylene glycol. Here, examples of the organic solvent include aliphatic hydrocarbons such as hexane and heptane, cycloaliphatic hydrocarbons such as cyclohexane and methylcyclohexane, aromatic hydrocarbons such as toluene and xylene, ethers such as diethyl ether and dibutyl ether, organic chlorides such as methylene chloride and chloroform, esters such as ethyl acetate and butyl acetate and ketones such as methyl isobutyl ketone, and, among these, cycloaliphatic hydrocarbons are preferable, and methylcyclohexane is more preferable from the viewpoint of impurity removal. These organic solvents may be used singly or two or more organic solvents may be selected, mixed in an arbitrary ratio and used. The amount of the organic solvent used is preferably 10 to 300 parts by mass and more preferably 20 to 200 parts by mass with respect to 100 parts by mass of the crude 1,3-butylene glycol from the viewpoint of the extraction efficiency.

The amount of water used is preferably 20 to 400 parts by mass and more preferably 40 to 200 parts by mass with respect to 100 parts by mass of the crude 1,3-butylene glycol from the viewpoint of the extraction efficiency. The order of adding water and the organic solvent to the crude 1,3-butylene glycol is not particularly limited. The temperature at which water and the organic solvent are mixed with the crude 1,3-butylene glycol is not particularly limited, but is preferably a temperature of 5° C. to 80° C. and more preferably a temperature of 10° C. to 50° C. from the viewpoint of the extraction efficiency.

The crude 1,3-butylene glycol, water and the organic solvent can be mixed by, for example, a batch method, a continuous method or the like.

Examples of the case of mixing by a batch method include a form in which the crude 1,3-butylene glycol, water and the organic solvent are put into a mixing tank, preferably stirred for 10 seconds to two hours and then preferably placed still for one minute to two hours to be phase-separated and a water layer containing 1,3-butylene glycol is obtained and the like. After the obtained water layer containing 1,3-butylene glycol is phase-separated by further adding the organic solvent, the operation of obtaining the water layer containing 1,3-butylene glycol may be repeated, and the number of repetitions is preferably once to three times. In this case, the amount of the organic solvent added per operation is preferably 10 to 300 parts by mass with respect to 100 parts by mass of the crude 1,3-butylene glycol.

As a device in the case of mixing by a continuous method, devices that are ordinarily used for continuous extraction or the like, for example, a combination of a mixer and a settler, a spray tower, a packed tower, a tray tower and the like can be used, and, in particular, a packed tower or tray tower having three or more theoretical plates is preferably used.

Hydrolysis Step

The hydrolysis step in the production method of the product 1,3-butylene glycol of the present embodiment is a step of performing a heating treatment on the water layer containing 1,3-butylene glycol obtained in the extraction step. When a heating treatment is performed on the water layer containing 1,3-butylene glycol, acetal compounds or the like that are contained in the water layer are hydrolyzed to turn into low-boiling point substances, and thus it is presumed that the low-boiling point substances that act as odor causes and coloration causes under a basic condition are efficiently removed in the subsequent distillation step. However, the mechanism of the present invention is not limited to what has been described above.

The heating time in the hydrolysis step is not particularly limited, but is preferably 20 minutes to nine hours, more preferably one to six hours and still more preferably one to three hours. When the heating time is 20 minutes or longer, there is a tendency for the hydrolysis of the acetal compounds or the like to sufficiently progress, and, when the heating time is nine hours or shorter, there is a tendency that the cost taken for the heating treatment can be suppressed.

The heating temperature in the hydrolysis step is not particularly limited, but is preferably 60° C. to 130° C., more preferably 75° C. to 115° C. and still more preferably 90° C. to 100° C. When the heating temperature is 60° C. or higher, there is a tendency for the hydrolysis of the acetal compounds or the like to sufficiently progress, and, when the heating temperature is 130° C. or lower, there is a tendency that the vaporization of water from the water layer containing 1,3-butylene glycol is suppressed and the hydrolysis rate of the acetal compounds or the like can be maintained.

A heating treatment device in the hydrolysis step is not particularly limited, examples thereof include heating treatment devices such as a continuous tube-type device, a batch tank-type device and a continuous tank-type device, and, in a case where the batch method is used, the batch tank-type device is particularly preferable from the viewpoint of the stirring efficiency.

Dehydration with Distillation Step

The dehydration with distillation step in the production method of the product 1,3-butylene glycol of the present embodiment is a step of distilling water away from the water layer containing 1,3-butylene glycol obtained in the hydrolysis step. Examples of a distillation device that is used in the dehydration with distillation step include a perforated plate tower, a bubble cap tower and a packed tower, and, among these, a packed tower having seven to 40 theoretical plates is preferable. The distillation tower may be one tower, or two or more towers may be used. As the distillation conditions, the pressure at the tower top portion of the distillation tower is preferably 5 to 20 kPa, and the temperature at the tower bottom portion of the distillation tower is preferably 120° C. to 160° C. and more preferably 135° C. to 155° C. Examples of a specific aspect of the dehydration with distillation step include a method in which the water layer containing 1,3-butylene glycol is continuously supplied from the tower top of the distillation tower, a distillate containing a large amount of water is continuously extracted from the tower top and, simultaneously, 1,3-butylene glycol is continuously extracted from the tower bottom.

Low-Boiling Fraction Distillation Step

The low-boiling fraction distillation step in the production method of the 1,3-butylene glycol of the present embodiment is a step of distilling the low-boiling point components away from 1,3-butylene glycol obtained in the dehydration with distillation step. Examples of a distillation device that is used in the low-boiling fraction distillation step include a perforated plate tower, a bubble cap tower and a packed tower, and, among these, a packed tower having seven to 40 theoretical plates is preferable. The distillation tower may be one tower, or two or more towers may be used. As the distillation conditions, the pressure at the tower top portion of the distillation tower is preferably 1 to 20 kPa, and the temperature at the tower bottom portion of the distillation tower is preferably 100° C. to 160° C. and more preferably 110° C. to 140° C. Examples of a specific aspect of the low-boiling fraction distillation step include a method in which 1,3-butylene glycol is continuously supplied from the tower top of the distillation tower, a distillate containing a large amount of the low-boiling point components is continuously extracted from the tower top and, simultaneously, 1,3-butylene glycol is continuously extracted from the tower bottom.

As a production method of 1,3-butylene glycol in the present embodiment, a method in which the preferable ranges of the above-described individual steps are combined together is preferable.

EXAMPLES

Hereinafter, the present invention will be more specifically described with examples, but the present invention is not limited to the following examples. As crude 1,3-butylene glycol that acted as a raw material, 1,3-butylene glycol manufactured by KH Neochem Co., Ltd. (product name: 1,3-butylene glycol) was used. A variety of analyses and evaluations were performed according to the following.

HPLC Analysis

Under the following conditions, an HPLC analysis of a product 1,3-butylene glycol was performed.

Conditions of HPLC Analysis

Sample preparation: 1000 µL of a solution from which 2,4-dinitrophenylhydrazine had been extracted by adding 5 mL of acetonitrile to a 2,4-dinitrophenylhydrazine cartridge (InertSep mini AERO DNPH, GL Sciences Inc.) and 100 µL of 0.2 mol/L hydrochloric acid were added to 0.05 g of 1,3-butylene glycol and reacted at 45° C. for two hours. The reaction liquid was diluted to 2 mL with a mobile phase that was used in HPLC, and this diluted liquid was used as a measurement sample.

Analysis device: Agilent 1200 Series manufactured by Agilent Technologies, Inc.

Detector: Agilent 1200 Series UV-Vis detector G1314B manufactured by Agilent Technologies, Inc.

Detection wavelength: 369 nm

Analysis column: SUPELCO (R) Ascentis (R) RP-Amide (particle diameter: 5 µm, inner diameter×length=4.6 mm×25 cm) manufactured by Merck KgaA Analysis condition: Column temperature of 40° C.

Mobile phase: Acetonitrile/distilled water=50/50 (volume ratio)

Mobile phase flow rate: 0.4 mL/min.

Sample injection condition: 20

Calibration curve: Created using separately synthesized dinitrophenylhydrazine derivatives of 2-(hydroxyethyl)-2,6-dimethyl-1,3-dioxane SUPELCO (R) Ascentis (R) RP-Amide manufactured by Merck KGaA used as the analysis column is a column in which palmitamidopropyl group-modified silica gel (particle diameter: 5 μm, inner diameter×length=4.6 mm×25 cm, pore size: 100 Å, surface coating level: 2.7 μmol/m$^2$, surface area: 450 m$^2$/g, metal impurity: less than 5 ppm, carbon content: 19.5%) is used as a stationary phase.

In the measurement of the sample prepared by the above-described method, the absorbance at 369 nm of the peaks of the dinitrophenylhydrazine derivatives of 2-(hydroxyethyl)-2,6-dimethyl-1,3-dioxane was measured with an ultraviolet spectrophotometer. The sum of the obtained absorbance was converted to the weight proportion of the dinitrophenylhydrazine derivatives of 2-(hydroxyethyl)-2,6-dimethyl-1,3-dioxane in 1,3-butylene glycol using "peak sum weight proportion (ppm)=0.206×sum of absorbance", which was a formula derived with the calibration curve. When the relative retention time of the peak of DNPH was regarded as 1.0, peaks that appeared within a relative retention time range of 1.1 to 1.6 (peaks A and B in FIG. 1) were regarded as the peaks of the dinitrophenylhydrazine derivatives of 2-(hydroxyethyl)-2,6-dimethyl-1,3-dioxane.

Gas Chromatography Analysis

Under the following conditions, a gas chromatography analysis of the product 1,3-butylene glycol, which was a subject, was performed.

Conditions of Gas Chromatography Analysis

Analysis device: 7890B gas chromatography system manufactured by Agilent Technologies, Inc.

Analysis column: DB-WAX (length 30 m×inner diameter 0.25 mm×film thickness 0.25 μm) manufactured by Agilent Technologies, Inc.

Temperature rising conditions: The temperature was raised from 80° C. up to 230° C. at 5° C./minute and then retained at 230° C. for 10 minutes.

Sample introduction temperature: 250° C.

Carrier gas: Nitrogen

Gas flow rate in column: 0.5 mL/minute

Detector and detection temperature: Flame ionization detector (FID), 250° C.

Control mode: Constant flow

Split ratio: 50:1

Sample injection condition: 1 μL

Odor Test

On 1,3-butylene glycol obtained in examples and comparative examples, an odor test was performed according to two evaluation methods described below.

Evaluation Method of Odor 10 g of a 10 weight % aqueous solution of 1,3-butylene glycol was put into a 20 mL wide mouth glass bottle, a lid was closed, and the aqueous solution was stirred hard at room temperature for one minute. The lid was opened, the odor was smelled and compared with a standard odor sample, and the odor level of the sample was determined. The number of evaluators was set to seven, and the average point of the evaluation results by the individual persons was calculated and used as a grade of the odor.

Evaluation Method of Odor Recurrence 10 g of a 10 weight % aqueous solution of 1,3-butylene glycol was put into a 20 mL wide mouth glass bottle, a lid was closed, and the aqueous solution was heated at 50° C. for three days. After that, the aqueous solution was cooled to room temperature and stirred hard for one minute. The lid was opened, the odor was smelled and compared with a standard odor sample, and the odor level of the sample was determined. The number of evaluators was set to seven, and the average point of the evaluation results by the individual persons was calculated and used as a grade of the odor recurrence. The above-described test will be referred to as the odor recurrence test.

Grades

A 10 weight % aqueous solution of 1,3-butylene glycol manufactured by KH Neochem Co., Ltd. was used as the standard odor sample, and the grade of the sample was determined as five. In a case where no odor was sensed, a grade 1 was given, and, in the other cases, grades 2 to 4 were given according to the following criteria.

1: No odor is sensed
2: An odor is faintly sensed
3: A weak odor is sensed
4: An odor is sensed
5: An odor is clearly sensed Basic Coloration Test On 1,3-butylene glycol obtained in examples and comparative examples, coloration under a basic condition was evaluated according to the following method.

Conditions of Basic Coloration Test 13 g of water and 2 g of potassium hydroxide were added to a 100 mL heat-resistant medium bottle and mixed together, and 6 g of 1,3-butylene glycol, which was a subject, was further added thereto. Next, the heat-resistant medium bottle was immersed in a water bath, and a heating treatment was performed at 90° C. for six hours. After a solution that had been subjected to the base treatment was cooled to room temperature, the color saturation (b*) of the solution was measured with a color difference meter SE2000 manufactured by Nippon Denshoku Industries Co., Ltd. The same operation was performed three times, and the average point of three measurement results was calculated and used as a grade of the color saturation (b*).

Example 1

Extraction Step 100 g of 1,3-butylene glycol manufactured by KH Neochem Co., Ltd., 100 g of water and 100 g of methylcyclohexane were charged into a 500 mL separable flask, stirred at a temperature set to 10° C. and a rotation speed of 500 rotations/minute for 10 minutes, then, placed still for five minutes and phase-separated into a water layer and an organic layer. 100 g of methylcyclohexane was further added to the separated water layer, and the same operation was repeated twice.

Hydrolysis Step

Next, the water layer obtained in the extraction step was charged into a three-neck flask equipped with a cooler, and a heating treatment was performed at an oil bath temperature of 100° C. for one hour.

Dehydration with Distillation Step

Next, the water layer that had been subjected to the heating treatment was charged into an eggplant flask and dehydrated and concentrated at an oil bath temperature of 150° C. and 8 kPa for 30 minutes, thereby obtaining 87 g of 1,3-butylene glycol.

Low-Boiling Fraction Distillation Step

Low-boiling fraction distillation were performed on 1,3-butylene glycol that had been subjected to the above-described dehydration and concentration with a distillation device equipped with a 20 cm Vigreux fractionator at an oil bath temperature of 120° C. and 1.2 kPa, and a distillate as much as a weight proportion of 3% of the amount of liquid charged from the distillation device top was distilled away. As a result, 77 g of a product 1,3-butylene glycol was obtained.

As a result of performing an HPLC analysis, in which the weight proportion was measured after a sample was prepared in advance, on the above-described product 1,3-butylene glycol, the peak sum weight proportion of dinitrophenylhydrazine derivatives of 2-(hydroxyethyl)-2,6-dimethyl-1,3-dioxane was 44 ppm. In addition, as a result of performing a gas chromatography analysis under the above-described conditions, the area percentage of the peak of 1,3-butylene glycol was 99.7%.

As a result of performing an odor test on the product 1,3-butylene glycol, the grade of the odor was one, and the grade of the odor recurrence was one. In addition, as a result of performing a basic coloration test, the color saturation (b*) after heating and holding at 90° C. for six hours under a basic condition was 4.1.

These results relating to the product 1,3-butylene glycol are shown in Table 1. In addition, the chart of the HPLC analysis of the product 1,3-butylene glycol in Example 1 is shown in FIG. 1.

Example 2

The steps, the analyses and the tests were performed in the same manner as in Example 1 except that the temperature in the extraction step was set to 50° C. As a result of performing an HPLC analysis, in which the weight proportion was measured after a sample was prepared in advance, on the obtained product 1,3-butylene glycol, the peak sum weight proportion of dinitrophenylhydrazine derivatives of 2-(hydroxyethyl)-2,6-dimethyl-1,3-dioxane was 35 ppm. In addition, as a result of performing a gas chromatography analysis under the above-described conditions, the area percentage of the peak of 1,3-butylene glycol was 99.7%.

As a result of performing an odor test on the product 1,3-butylene glycol, the grade of the odor was one, and the grade of the odor recurrence was one. In addition, as a result of performing a basic coloration test, the color saturation (b*) after heating and holding at 90° C. for six hours under a basic condition was 4.0.

These results relating to the product 1,3-butylene glycol are shown in Table 1.

Example 3

The steps, the analyses and the tests were performed in the same manner as in Example 1 except that the heating treatment time in the hydrolysis step was set to three hours. As a result of performing an HPLC analysis, in which the weight proportion was measured after a sample was prepared in advance, under conditions to be described below on the obtained product 1,3-butylene glycol, the peak sum weight proportion of dinitrophenylhydrazine derivatives of 2-(hydroxyethyl)-2,6-dimethyl-1,3-dioxane was 23 ppm. In addition, as a result of performing a gas chromatography analysis under the above-described conditions, the area percentage of the peak of 1,3-butylene glycol was 99.7%.

As a result of performing an odor test on the product 1,3-butylene glycol, the grade of the odor was one, and the grade of the odor recurrence was one. In addition, as a result of performing a basic coloration test, the color saturation (b*) after heating and holding at 90° C. for six hours under a basic condition was 3.9.

These results relating to the product 1,3-butylene glycol are shown in Table 1.

Example 4

The steps, the analyses and the tests were performed in the same manner as in Example 1 except that the oil bath temperature in the low-boiling fraction distillation step was set to 140° C. As a result of performing an HPLC analysis, in which the weight proportion was measured after a sample was prepared in advance, under conditions to be described below on the obtained product 1,3-butylene glycol, the peak sum weight proportion of dinitrophenylhydrazine derivatives of 2-(hydroxyethyl)-2,6-dimethyl-1,3-dioxane was 30 ppm. In addition, as a result of performing a gas chromatography analysis under the above-described conditions, the area percentage of the peak of 1,3-butylene glycol was 99.5%.

As a result of performing an odor test on the product 1,3-butylene glycol, the grade of the odor was one, and the grade of the odor recurrence was one. In addition, as a result of performing a basic coloration test, the color saturation (b*) after heating and holding at 90° C. for six hours under a basic condition was 3.4.

These results relating to the product 1,3-butylene glycol are shown in Table 1.

Example 5

The steps, the analyses and the tests were performed in the same manner as in Example 1 except that the heating time in the hydrolysis step was set to 30 minutes and a distillate as much as a weight proportion of 0.06% of the amount of liquid charged from the top of the distillation device was distilled away in the low-boiling fraction distillation step. As a result of performing an HPLC analysis, in which the weight proportion was measured after a sample was prepared in advance, under conditions to be described below on the obtained product 1,3-butylene glycol, the peak sum weight proportion of dinitrophenylhydrazine derivatives of 2-(hydroxyethyl)-2,6-dimethyl-1,3-dioxane was 75 ppm. In addition, as a result of performing a gas chromatography analysis under the above-described conditions, the area percentage of the peak of 1,3-butylene glycol was 99.7%.

As a result of performing an odor test on the product 1,3-butylene glycol, the grade of the odor was one, and the grade of the odor recurrence was two. In addition, as a result of performing a basic coloration test, the color saturation (b*) after heating and holding at 90° C. for six hours under a basic condition was 4.3.

These results relating to the product 1,3-butylene glycol are shown in Table 1.

Comparative Example 1

The steps, the analyses and the tests were performed in the same manner as in Example 1 except that the hydrolysis step and the low-boiling fraction distillation step were not performed and methyl isobutyl ketone was used as the extraction solvent in the extraction step. The details will be described below.

Extraction Step 100 g of 1,3-butylene glycol manufactured by KH Neochem Co., Ltd., 100 g of water and 100 g of methyl isobutyl ketone were charged into a 500 mL separable flask, stirred at a temperature set to 10° C. and a rotation speed of 500 rotations/minute for 10 minutes, then, placed still for five minutes and phase-separated into a water layer and an organic layer. 100 g of Methyl isobutyl ketone was further added to the separated water layer, and the same operation was repeated twice.

Dehydration with Distillation Step

Next, the water layer obtained in the extraction step was charged into an eggplant flask and dehydrated and concentrated at an oil bath temperature of 150° C. and 8 kPa for 30 minutes, thereby obtaining 79 g of 1,3-butylene glycol.

As a result of performing an HPLC analysis, in which the weight proportion was measured after a sample was prepared in advance, on 1,3-butylene glycol obtained in the dehydration with distillation step, the peak sum weight proportion of dinitrophenylhydrazine derivatives of 2-(hydroxyethyl)-2,6-dimethyl-1,3-dioxane was 98 ppm.

As a result of performing an odor test on the obtained 1,3-butylene glycol, the grade of the odor was three, and the grade of the odor recurrence was four. In addition, as a result of performing a basic coloration test, the color saturation (b*) after heating and holding at 90° C. for six hours under a basic condition was 4.6.

These results relating to 1,3-butylene glycol are shown in Table 1.

Figure 2:
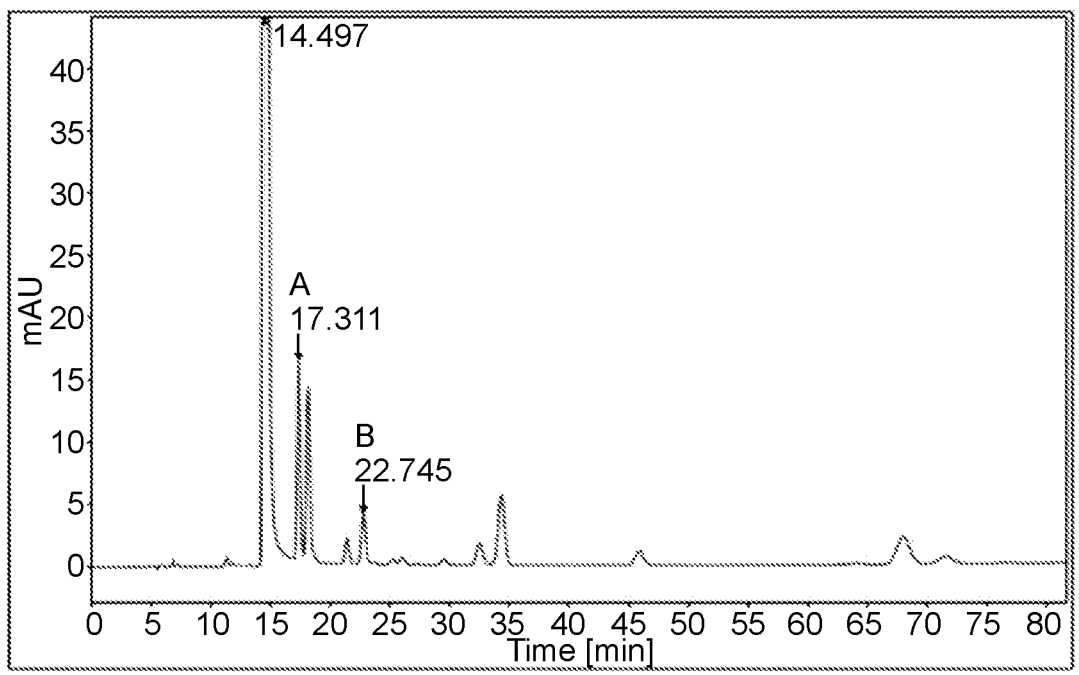
FIG. 2 is a chart of an HPLC analysis of 1,3-butylene glycol in Comparative Example 1 after being reacted by a 2,4-dinitrophenylhydrazine reagent in advance.

In addition, the chart of the HPLC analysis of 1,3-butylene glycol obtained in Comparative Example 1 is shown in FIG. 2.

TABLE 1

|  |  | Example 1 | Example 2 | Example 3 | Example 4 | Example 5 | Comparative Example 1 |
|---|---|---|---|---|---|---|---|
| HPLC analysis weight proportion (ppm) | | 44 | 35 | 23 | 30 | 75 | 98 |
| Odor test (grade) | Odor | 1 | 1 | 1 | 1 | 1 | 3 |
| | Odor recurrence | 1 | 1 | 1 | 1 | 2 | 4 |
| Basic coloration test | Color saturation (b*) | 4.1 | 4.0 | 3.9 | 3.4 | 4.3 | 4.6 |

The present application is based on a Japanese patent application filed on May 18, 2021 (Japanese Patent Application No. 2021-084070), the content of which is incorporated herein by reference.

INDUSTRIAL APPLICABILITY 1,3-Butylene glycol of the present invention is industrially available as a raw material of synthetic resins, a raw material of surfactants, a solvent, an antifreeze, a cosmetic raw material or the like.

The invention claimed is:

1. A product 1,3-butylene glycol, wherein 2,4-dinitrophenylhydrazine derivatives of 2-(hydroxyethyl)-2,6-dimethyl-1,3-dioxane have a weight proportion of from 23 ppm to 90 ppm, as calculated from a sum of absorbance of peaks thereof in an HPLC analysis under the following conditions after the following sample preparation, wherein the sample preparation is as follows:
1000 µL of a solution of 2,4-dinitrophenylhydrazine which is extracted by adding 5 mL of acetonitrile to a 2,4-dinitrophenylhydrazine cartridge and 100 µL of 0.2 mol/L hydrochloric acid are added to 0.05 g of the product 1,3-butylene glycol and reacted at 45° C. for two hours, and wherein the conditions of HPLC analysis are as follows:
Measurement sample: a reaction liquid obtained by the sample preparation is diluted to 2 mL with a mobile phase that is used in HPLC, and the diluted liquid is used as a measurement sample,
Detector: UV-Vis detector,
Detection wavelength: 369 nm,
Analysis column: a column in which palmitamidopropyl group-modified silica gel having particle diameter: 5 µm, inner diameter×length=4.6 mm×25 cm, pore size: 100 Å, surface coating level: 2.7 µmol/m$^2$, surface area: 450 m$^2$/g, metal impurity: less than 5 ppm, carbon content: 19.5%, is used as a stationary phase,
Analysis condition: column temperature of 40° C.,
Mobile phase: acetonitrile/distilled water=50/50 (volume ratio),
Mobile phase flow rate: 0.4 mL/min.,
Sample injection amount: 20 µL,
Calibration curve: created using separately synthesized dinitrophenylhydrazine derivatives of 2-(hydroxyethyl)-2,6-dimethyl-1,3-dioxane.

2. The product 1,3-butylene glycol according to claim 1, wherein the peaks of the 2,4-dinitrophenylhydrazine derivatives of 2-(hydroxyethyl)-2,6-dimethyl-1,3-dioxane have a weight proportion of from 23 ppm to 75 ppm, as calculated from the sum of the absorbance thereof.

3. The product 1,3-butylene glycol according to claim 1, wherein the 2,4-dinitrophenylhydrazine derivatives of 2-(hydroxyethyl)-2,6-dimethyl-1,3-dioxane have a weight proportion of from 23 ppm to 60 ppm, as calculated from the sum of the absorbance of the peaks.

4. A production method of the product 1,3-butylene glycol according to claim 1, comprising:
an extraction step of mixing the crude 1,3-butylene glycol with water and an organic solvent at a temperature of from 5° C. to 80° C., phase-separating the mixture into a water layer and an organic layer and then obtaining a water layer containing 1,3-butylene glycol,
a hydrolysis step of a heating the water layer containing 1,3-butylene glycol to a temperature of from 60° C. to 130° C. for from 20 minutes to 9 hours,
a dehydration with distillation step of distilling water away from the water layer containing 1,3-butylene glycol that has been subjected to the heating treatment and,
a low-boiling fraction distillation step of distilling low-boiling point components away from 1,3-butylene glycol from which water has been distilled away.

5. A production method of the product 1,3-butylene glycol according to claim 2, comprising:
an extraction step of mixing the crude 1,3-butylene glycol with water and an organic solvent at a temperature of from 5° C. to 80° C., phase-separating the mixture into a water layer and an organic layer and then obtaining a water layer containing 1,3-butylene glycol, a hydrolysis step of heating the water layer containing 1,3-butylene glycol to a temperature of from 60° C. to 130° C. for from 0.5 hours to 9 hours, a dehydration with distillation step of distilling water away from the water layer containing 1,3-butylene glycol that has been subjected to the heating treatment and, a low-boiling fraction distillation step of distilling low-boiling point components away from 1,3-butylene glycol from which water has been distilled away.

6. A production method of the product 1,3-butylene glycol according to claim 3, comprising:

an extraction step of mixing the crude 1,3-butylene glycol with water and an organic solvent at a temperature of from 5° C. to 80° C., phase-separating the mixture into a water layer and an organic layer and then obtaining a water layer containing 1,3-butylene glycol, a hydrolysis step of heating the water layer containing 1,3-butylene glycol to a temperature of from 60° C. to 130° C. for from 1 hour to 9 hours, a dehydration with distillation step of distilling water away from the water layer containing 1,3-butylene glycol that has been subjected to the heating treatment and, a low-boiling fraction distillation step of distilling low-boiling point components away from 1,3-butylene glycol from which water has been distilled away.

\* \* \* \* \*